(12) United States Patent
Zhao et al.

(10) Patent No.: US 8,968,727 B2
(45) Date of Patent: Mar. 3, 2015

(54) TELOMERASE ACTIVITY INHIBITING PEPTIDE AND MANUFACTURING METHOD AND APPLICATION THEREOF

(75) Inventors: Mujun Zhao, Shanghai (CN); Jian Feng, Shanghai (CN); Guoyuan Chen, Shanghai (CN); Jing Zhao, Shanghai (CN); Guangming Chen, Shanghai (CN); Liang Da, Shanghai (CN); Zaiping Li, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 13/808,059

(22) PCT Filed: Jul. 4, 2011

(86) PCT No.: PCT/CN2011/076806
§ 371 (c)(1),
(2), (4) Date: Jan. 2, 2013

(87) PCT Pub. No.: WO2012/000458
PCT Pub. Date: Jan. 5, 2012

(65) Prior Publication Data
US 2013/0108654 A1 May 2, 2013

(30) Foreign Application Priority Data
Jul. 2, 2010 (CN) .......................... 2010 1 0219318

(51) Int. Cl.
*A61K 38/44* (2006.01)
*C07K 14/47* (2006.01)
*C12N 9/12* (2006.01)
*A61K 38/00* (2006.01)

(52) U.S. Cl.
CPC ................ *C07K 14/47* (2013.01); *A61K 38/00* (2013.01); *C12N 9/1241* (2013.01); *C12N 9/1276* (2013.01); *C12Y 207/07049* (2013.01); *C07K 2319/00* (2013.01); *C07K 2319/10* (2013.01); *C07K 2319/23* (2013.01); *C07K 2319/30* (2013.01); *C07K 2319/31* (2013.01)
USPC ....................................... 424/94.1

(58) Field of Classification Search
None
See application file for complete search history.

(56) References Cited

U.S. PATENT DOCUMENTS

2004/0142357 A1    7/2004   Lu et al.

FOREIGN PATENT DOCUMENTS

| CN | 1170928 C | 10/2004 |
|---|---|---|
| CN | 1948339 A | 4/2007 |
| CN | 101643511 A | 2/2010 |
| WO | 01/22920 A2 | 4/2001 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Chen et al. (Gastroenterology, 140:332-343, 2011, available online Sep. 6, 2010).*
International Search Report issued in PCT/CN2011/076806 mailed Oct. 13, 2011 (8 pages).
Written Opinion issued in PCT/CN2011/076806 mailed Oct. 13, 2011 (9 pages).
Zhou, Xiao Zhen, et al.; "The Pin2/TRF1-Interacting Protein PinX1 is a Potent Telomerase Inhibitor"; Cell, vol. 107, Nov. 2, 2001; pp. 347-359.
Kim, Nam W., et al., "Specific Association of Human Telomerase Activity with Immortal Cells and Cancer"; Science, vol. 266, Dec. 23, 1994; pp. 2011-2015.
Liao, Cheng, et al., "Identification of the Gene for a Novel Liver-Related Putative Tumor Suppressor at a High-Frequency Loss of Heterozygosity Region of Chromosome 8p23 in Human Hepatocellular Carcinoma"; Hepatology, vol. 32, No. 4, Oct. 2000; The American Association for the Study of Liver Diseases, 0270-9139/00/3204-0007, doi: 10.1053/jhep.s000.17967; pp. 721-727.
Liao, Cheng, et al., "Mutation analysis of novel human liver-related putative tumor suppressor gene in hepatocellular carcinoma"; World Journal of Gastroenterology, vol. 9, No. 1, Jan. 15, 2003; The WJG Press ISSN 1007-9327; pp. 89-92.
Espacenet English Abstract for CN-101643511 (1 page), 2010.
Espacenet English Abstract for CN-1948339 (1 page), 2007.
Espacenet English Abstract for CN-1170928 (1 page), 2004.
Extended European Search Report dated Nov. 18, 2013, issued by the European Patent Office, Munich, Germany, in related European Patent Application No. 11800203.9 (6 pages).

* cited by examiner

*Primary Examiner* — Brian J Gangle
(74) *Attorney, Agent, or Firm* — Osha Liang LLP

(57) ABSTRACT

The present invention provides a telomerase activity inhibiting polypeptide. The expression of the polypeptide in tumor cells can inhibit significantly tumor cell telomerase activity, tumor cell growth, and lead to the death of such cells. The present invention further provides a preparation method for the polypeptide and an application thereof in targeted treatments of tumors.

16 Claims, 2 Drawing Sheets

SEQUENCE LISTING

<160> NUMBER OF SEQ ID NOS: 10

<210> SEQ ID NO 1
<211> LENGTH: 39
<212> TYPE: PRT
<213> ORGANISM: Homo sapiens

<400> SEQUENCE: 1

Thr Leu Lys Pro Lys Lys Arg Arg Gly Lys Lys Leu Gln Lys Pro
1               5                   10                  15

Val Glu Ile Ala Glu Asp Ala Thr Leu Glu Glu Thr Leu Val Lys Lys
            20                  25                  30

Lys Lys Lys Lys Asp Ser Lys
        35

<210> SEQ ID NO 2
<211> LENGTH: 328
<212> TYPE: PRT
<213> ORGANISM: Homo sapiens

<400> SEQUENCE: 2

Met Ser Met Leu Ala Glu Arg Arg Lys Gln Lys Trp Ala Val Asp
1               5                   10                  15

Pro Gln Asn Thr Ala Trp Ser Asn Asp Asp Ser Lys Phe Gly Gln Arg
            20                  25                  30

Met Leu Glu Lys Met Gly Trp Ser Lys Gly Lys Gly Leu Gly Ala Gln
            35                  40                  45

Glu Gln Gly Ala Thr Asp His Ile Lys Val Gln Val Lys Asn Asn His
    50                  55                  60

Leu Gly Leu Gly Ala Thr Ile Asn Asn Glu Asp Asn Trp Ile Ala His
65                  70                  75                  80

Gln Asp Asp Phe Asn Gln Leu Leu Ala Glu Leu Asn Thr Cys His Gly
                85                  90                  95

Gln Glu Thr Thr Asp Ser Ser Asp Lys Lys Glu Lys Lys Ser Phe Ser
            100                 105                 110

Leu Glu Glu Lys Ser Lys Ile Ser Lys Asn Arg Val His Tyr Met Lys
            115                 120                 125

Phe Thr Lys Gly Lys Asp Leu Ser Ser Arg Ser Lys Thr Asp Leu Asp
            130                 135                 140

Cys Ile Phe Gly Lys Arg Gln Ser Lys Lys Thr Pro Glu Gly Asp Ala
145                 150                 155                 160

Ser Pro Ser Thr Pro Glu Asn Glu Thr Thr Thr Ser Ala Phe
                165                 170                 175

Thr Ile Gln Glu Tyr Phe Ala Lys Arg Met Ala Ala Leu Lys Asn Lys
            180                 185                 190

Pro Gln Val Pro Val Pro Gly Ser Asp Ile Ser Val Thr Gln Val Glu
            195                 200                 205

Arg Lys Arg Gly Lys Lys Arg Asn Lys Glu Ala Thr Gly Lys Asp Val
    210                 215                 220

Glu Ser Tyr Leu Gln Pro Lys Ala Lys Arg His Thr Glu Gly Lys Pro
225                 230                 235                 240

Glu Arg Ala Glu Ala Gln Glu Arg Val Ala Lys Lys Ser Ala Pro
                245                 250                 255

Ala Glu Glu Gln Leu Arg Gly Pro Cys Trp Asp Gln Ser Ser Lys Ala
            260                 265                 270

Ser Ala Gln Asp Ala Gly Asp His Val Gln Pro Pro Glu Gly Arg Asp

```
                    275                 280                 285
Phe Thr Leu Lys Pro Lys Lys Arg Arg Gly Lys Lys Lys Leu Gln Lys
            290                 295                 300
Pro Val Glu Ile Ala Glu Asp Ala Thr Leu Glu Glu Thr Leu Val Lys
305                 310                 315                 320
Lys Lys Lys Lys Lys Asp Ser Lys
                325

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
aggaattcat gtctatgctg gctgaacg                                         28

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
acgctcgagc tttggaatct ttcttcttct                                       30

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
aggaattcac cctgaagccc aaaaagagg                                        29

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
acgctcgagc tttggaatct ttcttcttct tct                                   33

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
acgctcgaga aggatctgtc atctcgg                                          27

<210> SEQ ID NO 8
<211> LENGTH: 18
<212> TYPE: DNA
<213> ORGANISM: Artificial Sequence
<220> FEATURE:
<223> OTHER INFORMATION: Primer
```

```
<400> SEQUENCE: 8
aatccgtcga gcagagtt                                                        18

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gcgcggccct taccctacc cttaccctaa                                            30

<210> SEQ ID NO 10
<211> LENGTH: 36
<212> TYPE: DNA
<213> ORGANISM: Artificial Sequence
<220> FEATURE:
<223> OTHER INFORMATION: probe

<400> SEQUENCE: 10
ttagggttag ggttagggtt agggttaggg ttaggg                                    36
```

TELOMERASE ACTIVITY INHIBITING PEPTIDE AND MANUFACTURING METHOD AND APPLICATION THEREOF

BACKGROUND OF INVENTION

1. Field of the Invention

The present invention relate to the field of biotechnology and molecular biology research. The present invention relates to peptides highly efficient in inhibiting telomerase activity and methods of preparation and uses thereof.

2. Background Art

Telomerase is a ribonucleoprotein for synthesizing and extending chromosome telomeres in cells. It contains two basic components: a reverse transcriptase catalytic subunit hTERT and an RNA component hTR. Telomerase can use its own RNA as a template to reverse transcribe and synthesize telomere repeat sequences, which are added to the ends of chromosomes to compensate for the loss of telomeric DNA during cell divisions and maintain telomere lengths, Studies show that telomerase activity is almost undetectable in normal human cells. Therefore, the number of normal somatic cell division is limited. Telomeres are shortened 50-200 bp after every cell division. When telomeres are shortened to a certain degree, cell growth is inhibited, known as cellular senescence, leading to cell death. However, telomerase activities can be detected in the majority of malignant tumor cells (85%) and these activities are relatively high. The re-synthesis of telomere compensates for the continuous telomere loss during cell division processes and enables cells to divide continuously. This is an important mechanism for cell immortalization and tumorigenesis.

Kim et al., analyzed and summarized a large amount of research results, by examining more than 100 malignant tumor samples, and showed that the sensitivity of using telomerase in the diagnosis of tumor was 85%, specificity was 91%, the positive predictive value was 91%, and the negative predictive value was 81%. This fully demonstrates the value of using telomerase in diagnosis of tumors. (Kim N W, Piatyszek M A, Prowse K R, et al. Specific Association of human telomerase activity with immortal cells and cancer. Science. 1994 Dec. 23; 266 (5193): 2011-5.). Telomerase activation is considered a major factor for malignant tumor formation. The levels of activation and expression are closely associated with tumorigenesis and metastasis. Telomere shortening by inhibiting telomerase is considered a mechanism for cancer cell suppression. Thus, telomerase becomes an ideal target for targeted tumor therapy. Telomerase inhibitors for the treatment of tumors are being developed by many companies. Among these, GRN163L has begun a phase 2 clinical trial, and several telomerase vaccines will soon complete their clinical trials and enter the market.

LPTS (Liver Putative Tumor Suppressor) is a liver-related new candidate tumor suppressor gene obtained from normal human liver cDNA library using positional cloning approach by the inventors [C. Liao, M. J. Zhao, H. Song, K. Uchida, K. K. Yokoyama, T. P. Li, Identification of the gene for a novel liver-related putative tumor suppressor at a high-frequency loss of heterozygosity region of chromosome 8p23 in human hepatocellular carcinoma. Hepatology 2000, 32 721-727]. LPTS gene is located on human chromosome 8, region 8p23, which is lost at a high frequency in a variety of malignant tumor cells. Studies show that the expression levels of LPTS in hepatocellular carcinoma tissues and hepatoma cell lines are extremely low or undetectable. Introduction of LPTS gene into liver cancer cells can inhibit their growth, proliferation, and eventually induce liver cancer cell death. [Liao C, Zhao M J; Mutation analysis of novel human liver-related putative tumor suppressor gene in hepatocellular carcinoma. World J Gastroenterol, 2003, 9:89-93]. LPTS gene has been granted a patent in China in 2004 (Zhao Mujun et al.: "a liver cancer-related gene and use thereof," Patent No.: ZL 00115395.1, Patentee: Shanghai Institute of Biochemistry, Chinese Academy of Sciences; issued date: Oct. 13, 2004). In 2001, Dr. Lu's laboratory reported another full-length LPTS gene transcript PinX1 and found that PinX1 encoded protein can bind to the catalytic subunit of telomerase hTERT and inhibit telomerase activity [Zhou X. Z., Lu K. P; The Pin2/TRF1-interacting protein PinX1 is a potent telomerase inhibitor. Cell, 2001, 107, 347-359]. Based on this mechanism, it was proven, for the first time, that LPTS/PinX1 is a natural telomerase inhibitory protein that can inhibit tumor cell proliferation, providing a new way for targeted tumor therapy. In 2005, the present inventors submitted a patent application related to LPTS protein preparation (Zhao Mujun et al.: "Preparation and purification of telomerase activity inhibitory protein," Patent Application No.: 200510030526.5, filing date: Oct. 14, 2005; Applicant: Shanghai Institute for Biological Sciences, Chinese Academy of Sciences). That patent application provides a method for preparing the LPTS protein (LPGENE1) and an active telomerase inhibitory LPTS fragment LPTS133-328 (LPGENE2), and shows that the active LPTS telomerase inhibitory fragment is located at the C-terminal amino acid residues 133-328. A patent application submitted in 2008 by the present inventors showed that TAT and LPTS133-328 fusion protein (Patent Application Number: 200810041324.4) can pass through cell membranes and has an excellent efficacy in the inhibition of tumor cell growth.

Given that LPTS protein is an important protein closely associated with tumor cell growth, it is therefore necessary to further study LPTS and to develop more effective tumor inhibitory drugs to meet the need of clinical applications.

SUMMARY OF INVENTION

An objective of the present invention is to provide a polypeptide highly efficient in inhibiting telomerase activity and a method of preparation and a use thereof.

The first aspect of the present invention provides an isolated polypeptide (protein), said polypeptide is:
(a) a polypeptide having the amino acid sequence of SEQ ID NO:1;
(b) a polypeptide derived from (a) having one or more (for example, 1-10; preferably 1-5, more preferably 1-3) amino acid substitution, deletion, or insertion of the amino acid sequence of SEQ ID NO:1, and having the function of the polypeptide of (a); or
(c) a polypeptide derived from (a) having at least 90% (preferably 95%, more preferably 98%, and most preferably 99%) identity of the polypeptide sequence defined by (a) and having the function of the polypeptide of (a).

In another preferred embodiment, said polypeptide does not have the amino acid sequence of SEQ ID NO:2 (LPTS full-length sequence), the amino acid sequence at positions 133-328 of SEQ ID NO:2 (LPTS$_{133-328}$), and the amino acid sequence at positions 254-328 of SEQ ID NO:2.

In another preferred embodiment, said polypeptide includes the amino acid sequence at positions 255-328 of SEQ ID NO:2, or includes the amino acid sequence at positions 256-328 of SEQ ID NO:2, or includes the amino acid sequence at positions 257-328 of SEQ ID NO:2, or includes the amino acid sequence at positions 258-328 of SEQ ID NO:2, or includes the amino acid sequence at positions 259-

328 of SEQ ID NO:2, or includes the amino acid sequence at positions 260-328 of SEQ ID NO:2, or includes the amino acid sequence at positions 261-328 of SEQ ID NO:2, or includes the amino acid sequence at positions 262-328 of SEQ ID NO:2, or includes the amino acid sequence at positions 263-328 of SEQ ID NO:2, or includes the amino acid sequence at positions 264-328 of SEQ ID NO:2, or includes the amino acid sequence at positions 265-328 of SEQ ID NO:2, or includes the amino acid sequence at positions 266-328 of SEQ ID NO:2, or includes the amino acid sequence at positions 267-328 of SEQ ID NO:2, or includes the amino acid sequence at positions 268-328 of SEQ ID NO:2, or includes the amino acid sequence at positions 269-328 of SEQ ID NO:2, or includes the amino acid sequence at positions 270-328 of SEQ ID NO:2, or includes the amino acid sequence at positions 271-328 of SEQ ID NO:2, or includes the amino acid sequence at positions 272-328 of SEQ ID NO:2, or includes the amino acid sequence at positions 273-328 of SEQ ID NO:2, or includes the amino acid sequence at positions 274-328 of SEQ ID NO:2, or includes the amino acid sequence at positions 275-328 of SEQ ID NO:2, or includes the amino acid sequence at positions 276-328 of SEQ ID NO:2, or includes the amino acid sequence at positions 277-328 of SEQ ID NO:2, or includes the amino acid sequence at positions 278-328 of SEQ ID NO:2, or includes the amino acid sequence at positions 279-328 of SEQ ID NO:2, or includes the amino acid sequence at positions 280-328 of SEQ ID NO:2, or includes the amino acid sequence at positions 281-328 of SEQ ID NO:2, or includes the amino acid sequence at positions 282-328 of SEQ ID NO:2, or includes the amino acid sequence at positions 283-328 of SEQ ID NO:2, or includes the amino acid sequence at positions 284-328 of SEQ ID NO:2, or includes the amino acid sequence at positions 285-328 of SEQ ID NO:2, or includes the amino acid sequence at positions 286-328 of SEQ ID NO:2, or includes the amino acid sequence at positions 287-328 of SEQ ID NO:2, or includes the amino acid sequence at positions 288-328 of SEQ ID NO:2, or includes the amino acid sequence at positions 289-328 of SEQ ID NO:2, or includes the amino acid sequence at positions 290-328 of SEQ ID NO:2.

Another aspect of the present invention provides an isolated polynucleotide, which contains a polynucleotide sequence. Said polynucleotide sequence encodes an above-described polypeptide.

Another aspect of the present invention provides a vector, which contains an above-described polynucleotide.

Another aspect of the present invention provides a genetically engineered host cell, which contains an above-described vector.

Another aspect of the present invention provides a method for preparing an above-described polypeptide, said method comprises:
(a) culturing an above-described host cell under a condition suitable for expression to produce a cell culture; and
(b) isolating said polypeptide from the cell culture.

Another aspect of the present invention provides a use of said polypeptide for the manufacture of a composition for inhibiting telomerase activity in cells.

In another preferred embodiment of the present invention, said composition is used for preventing a disease associated with abnormal activation of telomerase.

In another preferred embodiment of the present invention, said disease associated with abnormal activation of telomerase is tumor.

Another aspect of the present invention provides a composition. Said composition contains an above-described polypeptide and a material compatible with said polypeptide.

In another preferred embodiment of the present invention, the composition is a fusion protein, comprising an above-described polypeptide linked with at least one functional protein (preferably linking through peptide bonds). Said functional protein has 5-500 (preferably 5-300; more preferably 10-250) amino acids.

In another preferred embodiment of the present invention, said functional protein is selected from: a membrane-penetrating protein (such as transactivator protein TAT), a tag protein (such as GST protein), a reporter protein (such as GFP protein), human serum albumin (extending half-life), and human IgG1:Fc fragment (extending half-life).

In another preferred embodiment of the present invention, an above-described polypeptide is directly linked to said functional protein, or linking through a linker peptide. The length of said linker peptide is 1-20 amino acids, and preferably 2-10 amino acids. The amino acid sequence of said linker peptide may be: GGS.

In another preferred embodiment, said fusion protein does not have the amino acid sequence of SEQ ID NO:2 (LPTS full-length sequence), the amino acid sequence at positions 133-328 of SEQ ID NO:2 (LPTS$_{133-328}$), and the amino acid sequence at positions 254-328 of SEQ ID NO:2.

In another preferred embodiment, said composition contains a substance selected from the following: a protein activity promoter, a protein activity stabilizer, and a protein half-life extending preparation (such as PEG, PEG-liposomes).

Another aspect of the present invention provides a composition containing a safe and effective amount of an above-described polypeptide or an above-described composition, and a pharmaceutically acceptable carrier.

In another preferred embodiment, said composition is used for inhibiting telomerase activity in cells.

In another preferred embodiment, said composition is used for preventing and treating tumors having increased telomerase activity.

Another aspect of the present invention provides a method for preparing a composition, said composition inhibits telomerase activity in cells. Said method includes: mixing a safe and effective amount of an above-described polypeptide or said composition, and a pharmaceutically acceptable carrier.

Another aspect of the present invention provides a kit, kit contains an above-described polypeptide; or contains an above-described complex; or contains an above-described composition.

In another preferred embodiment, said kit is used for inhibiting telomerase activity in cells.

In another preferred embodiment, said kit is used for preventing tumors having increased telomerase activity.

Another aspect of the present invention provides a method for inhibiting telomerase activity in cells (preferably in vitro, preferably non-therapeutic), including administering to a subject an effective amount of said polypeptide; or said complex; or said composition.

As a result of the present disclosure, other aspects of the present invention would be apparent to one skilled in the art.

BRIEF DESCRIPTION OF DRAWINGS

FIG. 3A shows Western blot detection of GFP, GFP-LPTS, and GST-LPTS$_{290\text{-}328}$ expression in the stable transfectant cell lines GFP/7404, GFP-LPTS/7404, and GST-LPTS$_{290\text{-}328}$/7404, respectively. Rabbit anti-GFP antibody serves as detection probe. FIG. 3B shows growth curves of each stable cell line is graphed as determined by MTT method. FIG. 3C shows morphologies of GFP/7404 (panel a), GFP-LPTS/7404 (panel b), and GST-LPTS$_{290\text{-}328}$/7404 (panel c) in cell culture. Arrows in the figures indicate cells in the period of crisis and with the symptom of senescence. FIG. 3C (panel d) shows dead and detached GST-LPTS$_{290\text{-}328}$/7404 cells.

DETAILED DESCRIPTION

Figure 1:
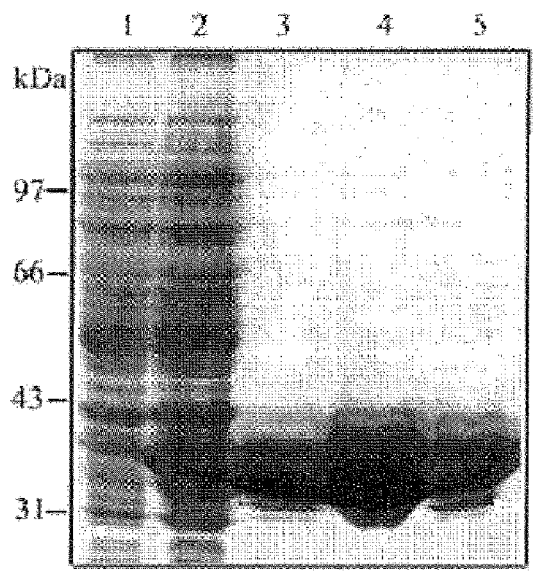
FIG. 1 shows induced expression and purification of GST-LPTS$_{290-328}$ fusion protein by SDS-PAGE. Lane 1 shows GST-LPTS$_{290-328}$ protein expressed by genetically engineered bacteria prior to IPTG induction. Lane 2 shows protein expressed by the engineered bacteria after IPTG induction. Lanes 3-5 show the purified GST-LPTS$_{290\text{-}328}$ protein collected into 3 tubes.

After thorough research, the present inventors, for the first time, isolated the active telomerase inhibitory domain of LPTS protein (the full-length sequence, such as SEQ ID NO: 2). The active domain is located at positions 290-328 of LPTS protein (LPTS$_{290\text{-}328}$). Activity of the active domain exceeds that of the full-length LPTS protein and other LPTS fragments and can induce faster tumor cell death. The present invention provides a more effective telomerase inhibitory protein in targeted tumor therapy.

Definitions

As used herein, "isolated" refers to materials isolated from their original environment (if it is a natural material, the original environment is the natural environment). For example, polynucleotides and polypeptides in natural condition of living somatic cells are not isolated and purified. However, the same polynucleotides and polypeptides separated from other co-existed components in the natural environment are isolated and purified.

As used herein, "subject," "individual," or "patient," refer to any target in need of diagnosis or treatment, especially mammalian subjects, especially human, other subjects include cattle, dogs, cats, guinea pigs, rabbits, rats, mice, horses, etc. Of particular concern is the subjects having abnormal telomerase activation.

As used herein, "nucleic acid" and "nucleic acid sequence" refers to nucleotides (ribonucleotide or deoxyribonucleotide) in polymeric form with any length. It includes (but not limited to) single-strand, double-strand DNA or RNA, genomic DNA and cDNA.

As used herein, "pharmaceutically acceptable" ingredients are materials suitable for use in human, and/or mammals without excessive adverse side effects (such as toxicity, irritation, and allergic reaction), and have a reasonable benefit/risk ratio. The term "pharmaceutically acceptable carrier" refers to therapeutic agent delivery carrier, including various excipients or diluent.

As used herein, "effective amount" or "safe and effective amount" refer to an amount of single agent or as a part of continuous agent given to individual for effective treatment or prevention. Said amount is determined based on health status and physiological condition of the treated individual, category of the treated individual (such as non-human primates, etc.), physician assessment of medical condition, and other related factors. Said amount can be estimated within a relatively wide range and can be determined by conventional experiments.

As used herein, the term "containing," "having" or "including" includes "containing," "mainly composed of," "basically composed of," and "composed of;" "mainly composed of," "basically composed of," and "composed of," belong to the subordinate concept of "containing," "having" or "including."

Polypeptides of the present invention and their encoding genes

LPTS is the first protein discovered capable of binding directly to human telomerase catalytic subunit hTERT and inhibiting telomerase catalytic activity. Based on the full-length LPTS protein, the present inventors predicts and screens a variety of LPTS sequence fragments. After repeated study and comparison, it is found that the active domain of LPTS protein for inhibiting telomerase activity can be narrowed down within a region of the protein at positions 290-328 of the amino acid sequence. This region is the critical domain for inhibiting telomerase activity, and is sufficient to inhibit telomerase activity, from which the polypeptide of the present invention was obtained.

To test the function of said polypeptide, the present inventors used genetic engineering technology to express GST-LPTS$_{290\text{-}328}$ fusion protein in vitro. In one embodiment of the present invention, TRAP (telomeric repeat amplification protocol) experimental technique was used to determine telomerase activity, and the in vitro inhibition of telomerase activity in tumor cells by GST-LPTS$_{290\text{-}328}$ fusion protein was detected. This method was based on PCR technique to detect telomerase activity and telomerase was obtained from a liver cancer cell lysate. Detection results showed that GST-LPTS$_{290\text{-}328}$ had a very strong telomerase inhibitory activity. Therefore, the present inventors further compared the activity of GST-LPTS$_{290\text{-}328}$ and GST-LPTS and GST-LPTS$_{133\text{-}328}$ proteins. Detection results showed GST-LPTS and GST-LPTS$_{133\text{-}328}$ proteins at 50 nM had telomerase inhibitory activity, and the inhibitory activity was stronger at 100 nM, but it could not completely inhibit telomerase in the reaction system. Whereas, GST-LPTS$_{290\text{-}328}$ already had very strong inhibitory activity at 50 nM, and could completely inhibit telomerase activity in the reaction system at 100 nM. The above results indicate LPTS$_{290\text{-}328}$ has a stronger telomerase inhibitory activity than the full-length LPTS and LPTS$_{133-328}$, representing the functional domain of LPTS that inhibits telomerase activity.

To detect the inhibitory activity of LPTS$_{290-328}$ in tumor cells in vivo, in one embodiment of the present invention, eukaryotic expression plasmids containing fusions of LPTS$_{290-328}$, LPTS and green fluorescent protein GFP, i.e., GFP-LPTS$_{290-328}$ and GFP-LPTS, were constructed. BEL7404 liver cancer cells were transfected with GFP-LPTS$_{290-328}$, GFP-LPTS, and the control GFP expression plasmids, respectively. After two weeks of G418 selection, flow cytometry FACS was used to sort out the cells expressing green fluorescent protein, followed by culturing. The selected and obtained GFP-LPTS$_{290-328}$/7404, GFP-LPTS/7404, and GFP/7404 cells were subjected to Western blot detection using rabbit anti-GFP polyclonal antibodies. It was found that cells all stably expressed the corresponding proteins. In the cell culturing process, the growth of GFP-LPTS$_{290-328}$/7404 cells was slower than that of GFP-LPTS/7404 and GFP/7404 cells. The present inventors performed MTT experiments on the above selected stable cell lines, which were selected by FACS and multiplied for 5 generations, and graphed growth curves. The results proved that, as compared with the control GFP/7404 cells, the growth of GFP-LPTS$_{290-328}$/7404 cells was the slowest, and GFP-LPTS/7404 the second. It indicates that the ability of LPTS$_{290-328}$ to inhibit tumor cell growth is stronger than that of the full-length LPTS. Overexpression of LPTS protein in tumor cells could lead to slow cell growth, flat morphology, entrance to crisis, and finally death. However, that was a long-term effect, and generally appeared after 6 weeks of culturing. After cells transfected with LPTS$_{290-328}$, death occurred quickly. After two weeks of G418 selection, only a few cells can be obtained for FACS selection. After culturing the obtained LPTS$_{290-328}$/7404 cells for about 10 days, senescence appeared, and they soon died after became rounded and detached from the plate. These results indicate that the ability of LPTS$_{290-328}$ overexpression to induce tumor cell death is very strong, and may have a higher efficiency in tumor inhibition than that of the full-length LPTS protein, thus, having more practical value.

In one embodiment of the present invention, to prove that LPTS$_{290-328}$ inhibits tumor cells by targeted inhibition of telomere synthesis in cells, Southern blot method was used to detect the telomere length of GFP-LPTS$_{290-328}$/7404, GFP-LPTS/7404, and GFP-7404 cells. Experimental results show that the telomeres of the control GFP-7404 cells remained constant during cell passage with a length of about 4.5 kb. The telomeres of GFP-LPTS/7404 cells were gradually shortened during cell passage with the telomeres shortened to about 3.8 kb, when cultured to the 5$^{th}$ generation; the telomeres shortened to about 2.8 kb, at the 25$^{th}$ generation. GFP-LPTS$_{290-328}$/7404 cells had a short passage time, many cells died during cell culture, the telomere shortened to about 2.5 kb at the 8$^{th}$ generation. These results indicate that LPTS$_{290-328}$ has a very strong telomerase inhibitory activity, which can inhibit the synthesis and extension of the telomere in vivo, and is a tumor inhibitory peptide for targeted telomerase inhibition.

Because the present invention reveals the most critical region for inhibiting telomerase catalytic activity, it is, therefore, understood that some proteins (such as some fusion proteins containing the polypeptide of the present invention), as long as they contain the most critical region and do not contain any factor that may affect the structure and the activity of the critical region (can be conveniently tested through limited experimentation), would also have the effect of inhibiting telomerase catalytic activity. These proteins are also included in the present invention.

Polypeptides of the present invention may be recombinant polypeptides, natural polypeptides, synthetic polypeptides, and preferably recombinant polypeptides. Polypeptides of the present invention may be purified natural products, chemically synthesized products, or produced by recombinant technology from prokaryotic or eukaryotic host cells (for example, bacteria, yeast, higher plants, insects, and mammalian cells). According to the host cells used for recombinant production, polypeptides of the present invention may be glycosylated or non-glycosylated. Polypeptides of the present invention may or may not include the starting methionine residue.

The present invention also includes fragments of said polypeptides, derivatives, and analogs. As used herein, the terms "fragments," "derivatives," and "analogs," refer to polypeptides that maintain basically the similar biological function and the activity as that of the polypeptides of the present invention. The fragments, derivatives, or analogs of the polypeptides may be (i) polypeptides substituted by one or more conservative or non-conservative amino acid residue (preferably conservative amino acid); or (ii) polypeptides having one or more amino acid having substituents; or (iii) polypeptides formed by fusion of mature polypeptides with another compound (for example, polypeptide half-life extending compound, such as polyethylene glycol); or (iv) polypeptides formed by fusing additional amino acid sequences with said polypeptide sequences (such as fusion proteins formed with leader sequences, secretory sequences, sequences used for purifying said polypeptides or the original protein sequences, or with IgG fragments). According to the teaching of the current disclosure, these fragments, derivatives, and analogs belong to the common knowledge of one skilled in the art.

The present invention also includes variants of SEQ ID NO: 1 having similar function as that of said polypeptides. These variants include (but not limited to): deletion, insertion, and/or substitution of one or more (usually 1-10, preferably 1-5, more preferably 1-3, and most preferably 1-2) amino acid, and addition of one or more (usually less than 10, preferably less than 5, and most preferably less than 3) amino acid at the C-terminus and/or N-terminus. For example, in the present field, substitution with amino acids having close or similar functions usually does not alter the protein function. For instance, addition of one or more amino acid at the C-terminus and/or the N-terminus usually does not alter protein function. Said terms also include active fragments and active derivatives of said polypeptides.

Polypeptide variants include: homologous sequences, conservative variants, allelic variants, natural mutants, induced mutants, the proteins whose DNA coding sequences can hybridize with that of the said polypeptides under high or low stringencies, and polypeptides or proteins obtained by using anti-said polypeptides antiserum. The present invention also provides other polypeptides, such as fusion proteins containing said polypeptides or their fragments.

The present invention also provides said polypeptides or analogs of said polypeptides. The differences between these analogs and natural said polypeptides may be the differences in amino acid sequences, and may be differences in modification that do not affect the sequences, or both. These polypeptides include natural or induced genetic variants. Induced variants may be obtained through various techniques, such as through radiation or exposure to mutagens to generate random mutagenesis, and through site-directed mutagenesis or other known molecular biology techniques. Analogs also include analogs having residues different from natural L-amino acids (such as D-amino acids), and analogs having unnatural or synthetic amino acids (such as β- and γ-amino acids). It should be understood that polypeptides of the present invention are not limited to the polypeptides represented in the above examples.

Modifications (usually do not alter the primary structures) include: forms of chemical derivation of polypeptides in vivo and in vitro, such as acetylation or carboxylation. Modifications also include glycosylation, such as polypeptides produced in polypeptide synthesis and processing or in further processing steps of glycosylation modification. This kind of modifications can be accomplished by exposing polypeptides to glycosylation enzymes (such as mammalian glycosylation enzymes or de-glycosylation enzymes). Forms of modification also include sequences having phosphorylated amino acid residues (such as phosphor-tyrosine, phosphor-serine, and phosphor-threonine). They also include modified polypeptides with improved resistance to proteolysis or with enhanced solubility.

In the present invention, "conservative polypeptide variants of said polypeptides" refer to polypeptides, as compared with the amino acid sequence of SEQ ID NO: 1, generated by substitution of at most 10, preferably at most 5, and more preferably at most 3, and most preferably at most 2 amino acids having close or similar properties. It would be best if the conservative polypeptide variants are generated by substitution of amino acids according to Table 1.

TABLE 1

| Initial Residue | Representative Substitution | Preferred Substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Use of said polypeptides of the present invention includes (but not limited to): a direct use as drugs for treating diseases associated with abnormal telomerase activation (such as tumors).

Fusion molecules containing or coupled with said polypeptides are also included in the present invention. For example, fusion molecules of polypeptides of the present invention and target molecules can be constructed. This kind of fusion molecules, which contain targeting molecules for specific tissues or organs, can increase drug concentration in local areas without affecting other areas. Said targeting molecules are: for example, antibodies, ligands, etc. For instance, fusion molecules of polypeptides of the present invention and polymers can be constructed; the half-life of said fusion molecules increases; and said polymer is, for example, IgG Fc.

Fusion genes containing coding sequences for said polypeptides are also included in the present invention. For example, fusion genes having coding sequences of said polypeptides and tissue or organ specific promoters (both operably linked) can be constructed. After given into the body, said genes driven by the promoters can be expressed in specific tissues or organs.

The present invention also includes some compositions, which contain polypeptides of the present invention, and other functional proteins and molecules linked to or coupled with the polypeptides of the present invention. These functional proteins (having 5-500; preferably 5-300, more preferably 10-250 amino acids) include, but not limited to: membrane-penetrating proteins, GST proteins (purification tags), GFP proteins (reporter proteins), human serum albumin (extending half-life), human IgG1:Fc fragments (extending half-life), etc. Other molecules can also be selected from the following materials: protein activity promoters, protein activity stabilizers, and protein half-life extending preparations. Said protein half-life extending preparations are, for example, PEG (can be used to bond to the amino terminal or carboxyl terminal), PEG-liposome (can be used to encapsulate the polypeptides of the present invention). The molecular weight of said PEG may be 1000-50000; preferably 20000-40000.

As one embodiment of the present invention, said polypeptides can be fused with or coupled with molecules that can effectively penetrate cell membranes, thus, more conveniently to be introduced into cells and exerts the effects. Many known membrane-penetrating proteins include: transactivator protein TAT, Penetratin, peptides based on signal sequences, pVEC, Transportan, Amphiphilic model peptide, and Arg9, etc.

The polynucleotides of the present invention may be in the forms of DNA or RNA. DNA forms include cDNA, genomic DNA, or synthetic DNA. DNA may be single-strand or double-strand. DNA can be coding strands or non-coding strands.

The term "polynucleotides coding polypeptides" may include polynucleotides coding said polypeptides, and may also include polynucleotides having additional coding and/or non-coding sequences.

The present invention also relates to the above polynucleotide variants, coding for polypeptides identical to the amino acid sequences of the present invention or fragments, analogs, and derivatives of the polypeptides. Said polynucleotide variants may be naturally occurring allelic variants or unnatural occurring variants. These nucleotide variants include substitution variants, deletion variants, and insertion variants. As known in the art, allelic variants are in the form of polynucleotide substitution. It may have one or more nucleotide substitution, deletion, or insertion, but without substantially altering the function of the coded polypeptides.

The present invention also relates to polynucleotides hybridized with said sequences and the identity between two sequences is at least 50%, preferably at least 70%, more preferably at least 80%. The present invention specifically relates to polynucleotides that can hybridize with said polynucleotides of the present invention under strict conditions. In the present invention, "strict conditions" refers to: (1) hybridization and washing with lower ionic strength and at higher temperature, such as 0.2×SSC, 0.1% SDS, 60° C.; or (2) hybridization with denaturing agents, such as 50% (v/v) formamide, 0.1% calf serum/0.1% FICOLL (a neutral, highly branched, high mass, hydrophilic polysaccharide, prepared by reaction of the polysaccharide with epichlorohydrin), 42° C., etc; or (3) hybridization occurs only when the identity between two sequences is at least 90%, preferably more than 95%. In addition, polypeptides encoded by the hybridized polynucleotides share identical biological function and activity with that of the mature polypeptide shown by SEQ ID NO:2.

The present invention also relates to nucleic acid fragments that hybridize with said sequences. As used herein, the length of "nucleic acid fragments" contains at least 15 nucleotides, preferably at least 30 nucleotides, more preferably at least 50 nucleotides, and most preferably at least 100 nucleotides. Nucleic acid fragments can be used for nucleic acid amplification technique (such as PCR) to determine and/or isolate polynucleotides encoding said polypeptides of the present invention.

Polypeptides and polynucleotides of the present invention are provided preferably by isolation, more preferably by purification to homogeneity.

The full-length nucleotide sequences of the present invention or their fragments can be obtained usually by using PCR amplification, recombination, or synthesis methods. For PCR amplification method, primers may be designed according to the related nucleotide sequences disclosed by the present invention, especially the open reading frame sequences; and by using commercially available cDNA libraries or cDNA libraries prepared by one skilled in the art using conventional methods as templates to amplify and obtain the related sequences. When sequences are longer, it usually requires twice or more PCR amplification, and then splice together the amplified fragments according to the correct order.

Once the related sequences are obtained, recombination method can be used to obtain the related sequences in a large scale. They are usually cloned into vectors, then transfected into cells. The related sequences can then be obtained by isolating them from the proliferating host cells using conventional methods.

In addition, the related sequences can be synthesized, especially when the fragment length is short. Usually, first many small fragments are synthesized, and then spliced together to obtain fragments having very long sequences.

At present, DNA sequences encoding the proteins (or their fragments, or their derivatives) of the present invention of the present invention can be obtained by completely chemical synthesis. Then, said DNA sequences can be introduced into various currently available DNA molecules (or vectors) and into the cells known by one skilled in the art. In addition, mutations can be introduced into the protein sequences of the present invention through chemical synthesis.

DNA/RNA (Saiki, et al. Science 1985; 230:1350-1354) is amplified preferably by using PCR technique to obtain the genes of the present invention. Especially, when the full-length cDNA is difficult to obtain from the libraries, RACE method (RACE-cDNA terminal rapid amplification) can be preferably used. Primers used in PCR can be suitably selected according to the sequences of the present invention disclosed herein, and also can be synthesized using conventional methods. The amplified DNA/RNA fragments can be isolated and purified through conventional methods, such as gel electrophoresis.

Vectors and Cells

The present invention also relates to vectors containing polynucleotides of the present invention, and host cells generated by using vectors and coding sequences of the present invention through genetic engineering; and methods of preparing said polypeptides of the present invention by recombination technology.

Recombinant polypeptides of the present invention may be expressed or generated by using polynucleotide sequences of the present invention through conventional recombinant DNA technology (Science, 1984; 224: 1431). Generally speaking, they include the following steps:

(1) using the polynucleotides (or variants) coding for said polypeptides of the present invention or recombinant expression vectors containing said polynucleotides to transform or transfect suitable host cells;
(2) culturing host cells in suitable culture media; and
(3) isolating and purifying proteins from culture media or cells.

In the present invention, polynucleotide sequences of the present invention can be inserted into recombinant expression vectors. The term "recombinant expression vectors" refers to bacterial plasmids, bacteriophages, yeast plasmids, plant cell viruses, mammalian cell viruses, such as adenoviruses, retroviruses, or other vectors well known in the art. Any plasmids and vectors can be used, provided that they are stable and capable of replicating in host cells. One important feature of the expression vectors is that they usually contain replication origins, promoters, marker genes, and translation controlling elements.

Expression vectors containing polynucleotide sequences of the present invention and suitable transcription and translation controlling signals can be constructed by using methods well known to one skilled in the art. These methods include in vitro recombinant DNA technology, DNA synthesis technology, in vivo recombination technology, etc. Said DNA sequences can be effectively linked to suitable promoters on the expression vectors to direct mRNA synthesis. Representative examples of these promoters include: *E. coli* lac or trp promoter; λ bacteriophage $P_L$ promoter; eukaryotic promoters including CMV immediate early promoter, HSV thymidine kinase promoter, early and late SV40 promoter, retrovirus LTRs, and some other promoters known to control gene expression in prokaryotic or eukaryotic cells, or in their viruses. Expression vectors also include ribosome binding sites for translation initiation and translation terminator.

In addition, expression vectors preferably contain one or more selection marker genes used for phenotypic selection for the transfected host cells, such as, used in eukaryotic cells culture, dihydrofolate reductase, neomycin resistance, green fluorescence proteins (GFP), or *E. coli* tetracycline or ampicillin resistance.

Vectors containing said suitable DNA sequences and suitable promoters or controlling sequences can be used to transform suitable host cells, enabling them to express the proteins.

Host cells may be prokaryotic cells, such as bacterial cells; or lower eukaryotic cells, such as yeast cells; or higher eukaryotic cells, such as mammalian cells. Representative examples include: bacterial cells of *E. coli, Streptomyces*, and *Salmonella typhimurium* bacteria; eukaryotic cells, such as yeast; plant cells; *Drosophila* S2 or Sf9 insect cells; animal cells, CHO, COS, 293 cells, or Bowes melanoma cell, etc.

When polynucleotides of the present invention are expressed in higher eukaryotic cells, transcription can be increased if enhancer sequences are inserted into the vectors. Enhancers are DNA cis-acting factors and usually contain about 10 to 300 base pairs, acting on the promoters to increase gene transcription. Examples include SV40 replication origin late side of 100-270 base pairs enhancer, polyoma replication origin late side enhancer, and adenovirus enhancer, etc.

One skilled in the art would know how to select suitable vectors, promoters, enhancers, and host cells.

Recombinant DNA used to transform host cells may be performed by using conventional techniques well known to one skilled in the art. When host cells are prokaryotic cells, such as *E. coli*, the competent cells capable of absorbing DNA can be obtained after log phase growth, treated with $CaCl_2$. All of these steps are well known in the art. Another method uses $MgCl_2$. If necessary, transformation may be performed by using electroporation. When host cells are eukaryotic cells, the following DNA transfection methods can be selected: calcium phosphate co-precipitation, conventional mechanical methods, such as microinjection, electroporation, liposomal packaging, etc.

The obtained transformants can be cultured using conventional methods to express the polypeptides encoded by the genes of the present invention. Depending on the host cells used, culture media used in culturing can be selected from various conventional media. Culturing is performed under the conditions suitable for host cell growth. After host cells grow to a suitable cell density, promoters can be selectively induced by suitable methods (such as, temperature changes or chemical induction) and further culturing the cells for a period of time.

Recombinant polypeptides in the above methods can be expressed inside the cells or on the cell membranes, or secreted outside the cells. If necessary, recombinant proteins can be isolated and purified based on their physical, chemical, and other characteristics by various isolation methods. These methods are well known to one skilled in the art. Examples of these methods include, but not limited to: conventional renaturation treatments, protein precipitation agent treatments (salting-out methods), centrifugation, breaking-up bacteria by osmosis, super treatments, super centrifugation, molecular sieve chromatography (gel filtration), adsorption chromatography, ion exchange chromatography, high performance liquid chromatography (HPLC) and various other liquid phase chromatography techniques and a combination thereof.

As a specific embodiment of the present invention, $LPTS_{290-328}$ gene sequence is obtained mainly by PCR amplification using specifically designed primers and using pT-LPTS plasmid as a template. Insert $LPTS_{290-328}$ gene fragment into pGEX-4T-1 plasmid, which expresses GST fluorescence protein to obtain the pGEX-$LPTS_{290-328}$ recombinant plasmid. Transform the expression host bacterial cells *E. coli* BL-21(DE3) with the pGEX-$LPTS_{290-328}$ recombinant plasmid to obtain the engineered bacteria expressing GST-$LPTS_{290-328}$ fusion proteins. GST-$LPTS_{293-328}$ expression in *E. coli* is induced by IPTG. GST-$LPTS_{290-328}$ fusion protein purification can be performed by using the commercially available affinity purification column GS-4B.

Compositions

The present invention also provides various compositions containing polypeptides of the present invention, especially pharmaceutical compositions. Said compositions may be used to prevent or treat diseases associated with abnormal telomerase activation. Said disease includes (but not limited to): tumors.

Various compositions containing polypeptides of the present invention may include buffers selected according to the practical use of polypeptides; may also contain other substances suitable for the intended uses. One skilled in the art would be good at choosing suitable buffers. Many kind of buffers are known in the art and suitable for intended use. In some embodiments, said compositions may contain pharmaceutically acceptable excipients, which are many and known in the art without the need to further discuss in details here. Pharmaceutically acceptable excipients have been described in detail in many publications, such as "Remington's Pharmaceutical Sciences" ($19^{th}$ Edition (1995) Mack Publishing Co.).

Compositions of the present invention can be prepared to different formulations: injection, granules, tablet, pill, suppository, capsule, suspension, spray, suppository, transdermal drugs (such as patch, etc.), ointment, lotion, etc. Medicinal grade organic or inorganic carriers and/or diluents suitable for oral or topical use can be used for preparing various compositions containing active treatment compounds. Diluents known in the art include aqueous media, plant and animal oils and lipids. Stabilizers, wetting and emulsifying agents, osmotic pressure-changing salts, or various buffers that maintain suitable pH, and skin penetration enhancers can be used as auxiliary materials.

The conventionally and pharmaceutically acceptable ways of administering compositions of the present invention include: intramuscular, subcutaneous, intra-dermal, pulmonary, intravenous, intra-tumor, nasal, oral or other parenteral route of administration. If necessary, drug administrations can be combined or adjusted based on disease conditions. It can be given with single dose or multiple doses.

The amount of polypeptides is selected based on the amount capable of producing the effect of inhibiting telomerase activity without obvious side effect. Usually, it is given with about 0.01 μg-10 mg polypeptides/kg body weight, preferably 0.1 μg-1 mg polypeptides/kg body weight, and more preferably 0.1 μg-100 μg polypeptides/kg body weight.

Kits

The present invention also provides a kit for preventing diseases associated with abnormal telomerase activation. The kit contains polypeptides of the present invention or compositions containing said polypeptides. In addition, to facilitate drug delivery, said kit may also contain hypodermic needles, and/or pharmaceutically acceptable carriers, and/or user manuals.

Advantages of the Present Invention

1. First to discover that $LPTS_{290-328}$ has a very remarkable in vitro telomerase inhibitory activity, and is the strongest LPTS region known to possess telomerase inhibitory activity.

2. First to discover that heterologous expression of $LPTS_{290-328}$ can inhibit tumor cell growth, leading to telomere shortening in cells and finally death.

To further elaborate on the present invention, specific embodiments are combined as follows. It should be understood that these embodiments are only used to illustrate the present invention and are not used to limit the scope of the present invention. In the following embodiments, specific conditions not specified in the experimental methods are usually based on conventional conditions described in, such as Sambrook et al., Molecular Cloning: A Laboratory Guide (New York: Cold Spring Harbor Laboratory Press, 1989), or according to conditions recommended by the manufacturers.

Unless otherwise defined, all the professional and scientific terms used herein have the same meaning as that known by one skilled in the art. In addition, any methods and materials similar or equivalent to the present disclosure can also be used in the present invention. Preferred embodiments and methods described herein are only used for illustration.

Example 1

Preparation of $LPTS_{290-328}$ Gene Fragment

Construction of pT-LPTS plasmid: designed primer L1: 5'-AGGAATTCATGTCTATGCTGGCTGAACG-3'(SEQ ID NO: 3) and L2: 5'-ACGCTCGAGCTTTGGAATCTTTCT-TCTTCT-3'(SEQ ID NO: 4). Reverse transcription PCR amplification with said primers from normal liver tissues were used to obtain the full-length LPTS cDNA fragment. The PCR products were placed into pMD-18T vector (purchased from TaKaRa Company) to obtain pT-LPTS plasmid.

$LPTS_{290-328}$ gene fragment can be amplified by PCR method using pT-LPTS plasmid (said plasmid contains the full-length LPTS cDNA fragment). Designed PCR primer P1: 5'-AGGAATTCACCCTGAAGCCCAAAAAGAGG-3' (SEQ ID NO: 5) and P2: 5'-ACGCTCGAGCTTTG-GAATCTTTCTTCTTCTTCT-3'(SEQ ID NO: 6). Using pT-LPTS plasmid as a template and primers P1 and P2 to perform PCR reaction. PCR reaction conditions were: 94° C., 30 seconds, 55° C. annealing for 30 seconds, 72° C. extension for 30 seconds, and total 30 cycles of amplification. After DNA sequencing to confirm the amplified PCR products without mistake, the obtained $LPTS_{290-328}$ gene fragment was used to subsequently construct GST fusion proteins and eukaryotic expression vectors. The amino acid sequence coded by said $LPTS_{290-328}$ gene fragment is SEQ ID NO: 1.

$LPTS_{133-328}$ gene fragment, serving as a control, was obtained by using the same methods described above; PCR primers are P3: 5'-ACGCTCGAGAAGGATCTGT-CATCTCGG-3'(SEQ ID NO: 7) and P2. LPTS gene sequence was obtained by double digestion of pT-LPTS with EcoR I and Xho I. The protein encoded by said gene fragment corresponds to the full-length LPTS protein.

Example 2

Construction of $LPTS_{290-328}$ Fusion Protein Expression Engineered Bacteria and Induction Thereof $LPTS_{290-328}$ gene fragment and $LPTS_{133-328}$ gene fragment obtained in Embodiment 1 were double digested with EcoR I and Xho I, and then inserted into pGEX-4T-1 plasmid (purchased from Amersham Pharmacia Company), said plasmid was capable of expressing GST protein. LPTS gene fragment obtained in Embodiment 1 was directly inserted into pGEX-4T-1 plasmid to obtain pGEX-$LPTS_{290-328}$, pGEX-$LPTS_{133-328}$, and pGEX-LPTS recombinant plasmids. Host bacteria E. coli DH5α was transformed and the plasmid was then isolated from E. coli DH5α transformants. After sequencing to confirm no mistake, and then transformed the protein expression host bacteria E. coli BL-21 (DE3) to obtain pGEX-$LPTS_{290-328}$, pGEX-$LPTS_{133-328}$, and pGEX-LPTS fusion protein expression engineered bacterial clones.

Induced expression of GST-$LPTS_{290-328}$ in E. coli BL-21 (DE3). Fusion protein expression engineered bacteria containing pGEX-$LPTS_{290-328}$ plasmid were cultured at 37° C. overnight. On the second day, inoculating 400 ml LB culture media containing $Amp^r$ antibiotics according to 1:100 ratio. Continued culturing at 37° C. until OD600 at about 0.6 and add IPTG to a final concentration of 0.5 mM, and induced expression at 37° C. for 3-4 hours. Collecting bacteria by centrifugation at 5000 rpm for 10 minutes, removed supernatant, and stored the remaining bacteria at −80° C. Said bacteria contained the target GST-$LPTS_{290-328}$ fusion protein (see FIG. 1). Using similar methods, the present inventors induced the expression of GST-$LPTS_{133-328}$ and GST-LPTS fusion proteins. Structural diagram of GST and the fusion proteins described above are shown in FIG. 2A.

FIG. 1 shows the results of 10% SDS-PAGE gel electrophoresis after Coomassie brilliant blue staining. Lane 1 shows the engineered bacteria prior to IPTG induction. Lane 2 shows the engineered bacteria after IPTG induction, specific bands induced and located at 40 kD is GST-$LPTS_{290-328}$ protein.

Example 3

GST-$LPTS_{290-328}$ Fusion Protein Purification

GST-$LPTS_{290-328}$ fusion protein purification was performed by using commercially available affinity purification column GS-4B (purchased from Sigma Company). Said affinity purification column was reduced glutathione GSH coupled with Sepharose 4B. Before sample loading, first filled to a final volume of about 2 ml according to manufacture's instruction, and 20~30 ml solution A (20 mM Tris-HCl pH 7.4, 0.2 mM EDTA, 1 mM DTT, 0.5 mM PMSF, 1 M NaCl) was used to equilibrate. The previously obtained bacteria from Embodiment 2 were resuspended in 10 ml solution A. Ultrasonic crushing bacteria (ultrasound manufactured by Ningbo Xinzhi), ultrasound conditions were: working time 7 seconds, clearance time 25 seconds, power 400 W, working times 20-30 times). TRITON X-100 (polyethylene glycol p-(1,1,3,3-tetramethylbuytl)-phenyl ether)was added to the ultrasound-treated bacterial solution to a final concentration of 1%, and placed on ice for 30 minutes; then centrifuged at 12000 rpm, 4° C. for 10 minutes. The centrifuged supernatant was transferred to new centrifugation tubes and centrifugation was repeated. The supernatant containing fusion protein obtained from the repeated centrifugation was transferred to the equilibrated GS-4B purification column and was passed through the column with pressure differential. After sample passed through the column, the column was washed with 20~30 ml solution A; and then continued washing the column by using 20~30 ml solution B (20 mM Tris-HCl, pH 7.4, 0.2 mM EDTA, 0.1 M NaCl); and finally proteins were eluted using 5 ml solution C (15 ml reduced glutathione GSH, 20 mM Tris-HCl pH 7.4, 0.2 mM EDTA, 0.1 M NaCl); collected in total 3 tubes, each tube had approximately 1.5 ml, and the collection was stored purified protein at −80° C. The present inventors purified and obtained GST-$LPTS_{133-328}$ and GST-LPTS proteins using the same methods.

Lanes 3, 4, and 5 of FIG. 1 show the eluted proteins collected in 3 tubes. As can be seen, a single GST-$LPTS_{290-328}$ protein band was obtained after purification with a purity up to more than 95%, and can be used for further application. The concentration of the collected GST-$LPTS_{290-328}$ protein can be measured by Bradford method.

Example 4

Detection of the Telomerase Inhibitory Activity of GST-$LPTS_{290-328}$ Fusion Protein and Comparison of the Inhibitory Activity with GST-LPTS and GST-$LPTS_{133-328}$ Proteins To detect the telomerase inhibitory activity of GST-$LPTS_{290-328}$ fusion protein, the present inventors employed an in vitro TRAP experiment. TRAP (telomeric repeat amplification protocol) is a telomerase activity detection method based on PCR technique. First, preparing telomerase-containing BEL7404 liver cancer cell lysate. BEL7404 cells in the logarithmic vigorous growth period (purchased from the Chinese Academy of Sciences Shanghai Cell Bank) were washed twice with Washing Buffer (10 mM Hepes-KOH pH 7.5, 1.5 mM $MgCl_2$, 10 mM KCl, 1 mM DTT). Every $10^6$ cells were resuspended with 1 ml of ice cold Lysis Buffer (10 mM Tris-HCl pH 7.5, 1 mM MgCl$_2$, 1 mM EGTA, 0.1 mM PMSF, 5 mM mercaptoethanol, 0.5% CHAPS, 10% glycerol); lysed on ice for 30 minutes; then high-speed centrifuged at 15000 rpm, 4° C. for 30 minutes. The obtained supernatant was the telomerase-containing BEL7404 liver cancer cell lysate. The cell lysate can be stored in −80° C. refrigerator.

First, took 1 μl cell lysate for TRAP reaction, to which added GST-LPTS$_{290-328}$ protein or other proteins pending determination; mixed on ice for 10 minutes, then added 1 μl Ts primer (0.1 μg/μl, the sequence is 5'-AATCCGTCGAG-CAGAGTT-3'), 0.25 μl 10 mM dNTP, 42 μl reaction buffer (20 mM Tris-HCl pH 8.3, 1.5 mM MgCl$_2$, 63 mM KCl, 0.005% Tween-20, (Polyoxyethylene (20) sorbitan monolaurate), 1 mM EGTA, 0.1 mg/ml BSA), the above total volume was 50 μl. Then, extension reaction was performed at 25° C. for 30 minutes; inactivated at 90° C. for 3 minutes; and then added 1 μl Cx primer (the sequence is 5'-GCGCGG (CCCTTA)$_3$CCCTAA-3')(SEQ ID NO: 9), 0.5 μl (2 U) Taq enzyme, performed PCR reaction (94° C. for 40 seconds, annealing at 50° C., 40 seconds, 72° C. extension for 1 minute, and 30 cycles of amplification); and after the PCR products were isolated by 10% PAGE non-denaturing gel separation, silver staining was performed. More bands in the staining results indicate higher telomerase activity in the system, the opposite indicates greater inhibition of telomerase activity in the system.

Figure 2:
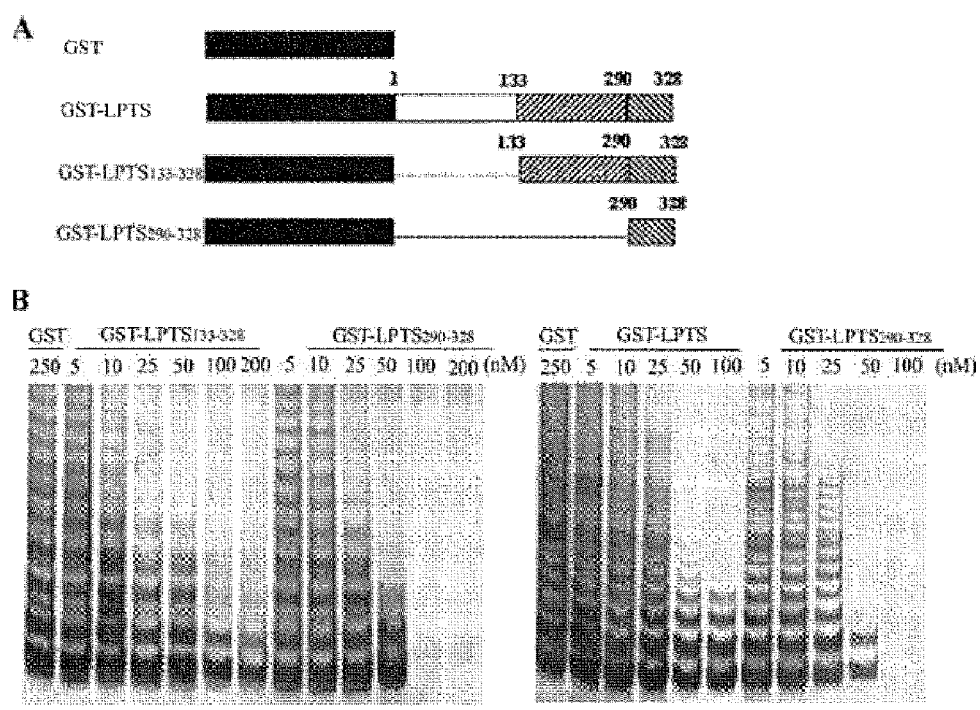
FIG. 2 shows detection and comparison in the telomerase inhibitory activity of GST-LPTS$_{290\text{-}328}$, GST-LPTS$_{133\text{-}328}$, and GST-LPTS. A. Structural diagram of GST-LPTS$_{290\text{-}328}$, GST-LPTS$_{133\text{-}328}$, and GST-LPTS. B. Detection of the telomerase inhibitory activity of GST-LPTS$_{290\text{-}328}$, GST-LPTS$_{133\text{-}328}$, and GST-LPTS by TRAP method. As shown in the figure, the amount of protein used is, respectively 5, 10, 25, 50, 100, 200, and 150 nM. GST protein serves as a control. Samples are detected by 10% PAGE non-denaturing gel electrophoresis, followed by silver staining to obtain results.

FIG. 2B shows the TRAP results. As can be seen, GST-LPTS and GST-LPTS$_{133-328}$ protein at 50 nM show telomerase inhibitory activity, a stronger inhibitory activity at 100 nM, but could not completely inhibit telomerase in the reaction system. Whereas, GST-LPTS$_{290-328}$ had a very strong inhibitory activity at 50 nM and completely inhibited telomerase activity in the system at 100 nM.

The above results show that LPTS$_{290-328}$ has a stronger telomerase inhibitory activity than that of the full-length LPTS and LPTS$_{133-328}$, and is a functional domain of the telomerase inhibitory activity of LPTS protein.

Example 5

LPTS$_{290-328}$ Inhibited BEL7404 Liver Cancer Cell Growth and Induced Cell Death To detect the in vivo tumor inhibitory activity of LPTS$_{290-328}$, the present inventors constructed eukaryotic expression plasmids of fusion of LPTS$_{290-328}$, LPTS and green fluorescent protein GFP. Specific operations as follows: LPTS$_{290-328}$ gene fragment obtained from Embodiment 1 was double digested with EcoR I and Xho I and then inserted into pEGFP-C2 plasmid (purchased from Clontech) to obtain pEGFP-LPTS$_{290-328}$ expression plasmid. pT-LPTS plasmid was double digested with EcoR I and Xho I to obtain LPTS gene cDNA fragment, and, similarly, inserted into pEGFP-C2 plasmid to obtain pEGFP-LPTS expression plasmid. pEGFP-C2 capable of expressing GFP protein served as a control. BEL7404 cells transfected with the above plasmids could express the corresponding proteins.

Figure 3:
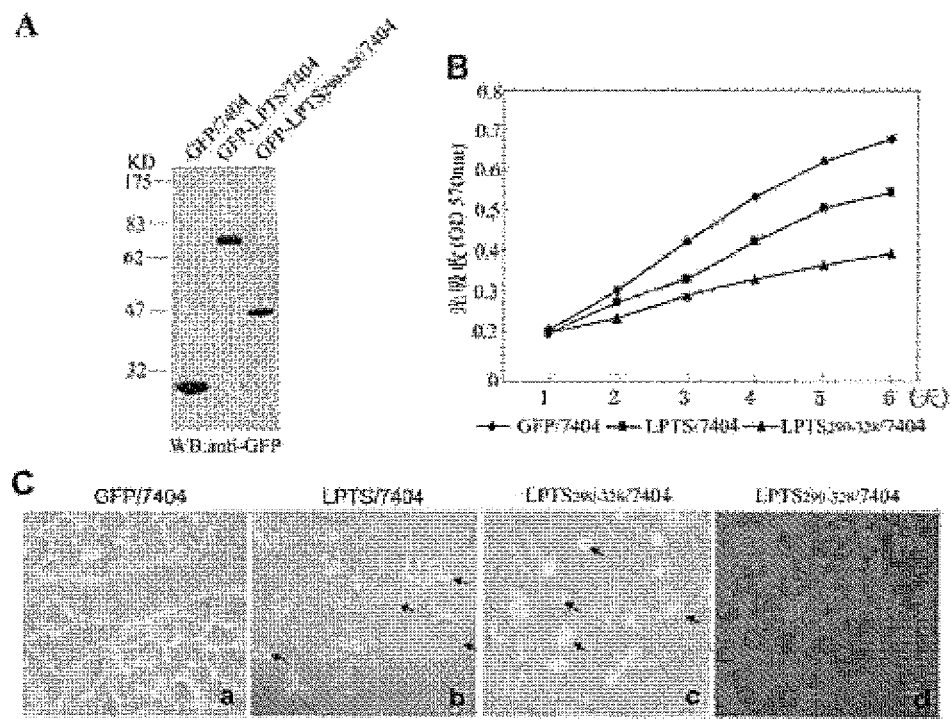
FIG. 3A-3C shows the effect of GST-LPTS$_{290\text{-}328}$ on the growth of BEL7404 liver cancer cells.

BEL7404 liver cancer cells were, respectively, transfected with GFP-LPTS$_{290-328}$, GFP-LPTS, and the control GFP expression plasmid. After G418 screening for 2 weeks, cells expressing green fluorescent protein were sorted out by using flow cytometry FACS, followed by cell culturing. As shown in FIG. 3A, all GFP-LPTS$_{290-328}$/7404, GFP-LPTS/7404, and GFP/7404 cells, obtained by sorting, stably expressed corresponding proteins as detected by Western blot using rabbit anti-GFP polyclonal antibody.

In cell culture, GFP-LPTS$_{290-328}$/7404 cells grew slower than GFP-LPTS/7404 and GFP/7404 cells. The present inventors performed MTT test to graph cell growth curves of the above FACS-sorted stable cell lines that had multiplied for 5 generations. As shown in FIG. 3B, results confirmed that GFP-LPTS$_{290-328}$/7404 cells had the slowest growth rate and the next were GFP-LPTS/7404 cells, as compared with the control GFP/7404 cells.

This result indicates that LPTS$_{290-328}$ has a stronger tumor growth inhibitory ability than the full-length protein LPTS.

Overexpressing LPTS protein in tumor cells can lead to slow cell growth, flattened morphology, entering the crisis period, and finally death. This is because LPTS protein inhibited the telomerase activity of tumor cells, causing telomeres not be able to extend and become shortened, leading to cellular senescence and death. But this is a long-term effect, and generally appeared after 6 weeks. However, cells transfected with LPTS$_{290-328}$, died soon after transfection. After 2 weeks of G418 selection, only a small number of cells were obtained for FACS sorting. As shown in FIG. 3C, the selected LPTS$_{290-328}$/7404 cells continued to be cultured for 10 days and then the symptoms of senescence appeared, and soon all rounded off, and then detached and died.

The above results show that LPTS$_{290-328}$ overexpression has a strong ability to induce tumor cell death and has a higher efficiency in tumor inhibition than the full-length LPTS protein, thus, having more application value.

Example 6

LPTS$_{290-328}$ Shortens the Telomere Length of BEL7404 Liver Cancer Cells

Figure 4:
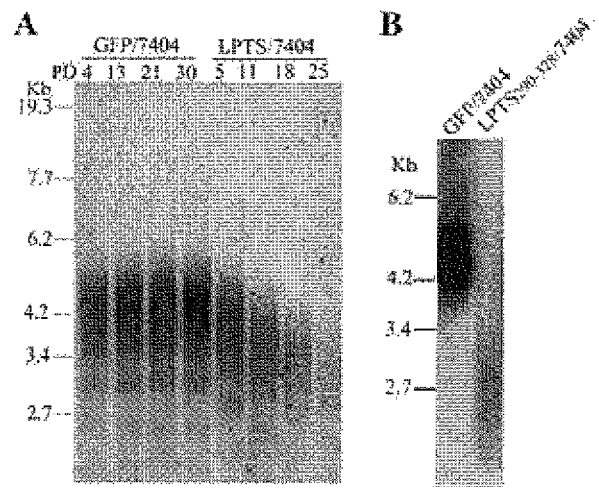
FIG. 4 shows the effect of LPTS and LPTS$_{290\text{-}328}$ on telomere length in BEL7404 liver cancer cells detected by Southern Blot experiment. A. BEL7404 cells transfected with GFP or GFP-LPTS were sorted by FACS, followed by continuous culturing. Cells were selected having different culture passage number (PD) as indicated in the figure. Isolating genomic DNA and digesting with Hinf I and Afa I endonucleases, followed by hybridization with a single-strand telomere repeat sequence $^{32}$P-(TTAGGG)$_6$ probe. B. GFP- or GFP-LPTS-transfected BEL7404 cells multiplied for 8 generations and then sorted out by FACS flow cytometry. Isolated genomic DNA and, after digestion with Hinf I and Afa I endonucleases, were hybridized with a single-strand telomere repeat sequence $^{32}$P-(TTAGGG)$_6$ probe. The figure shows the results after autoradiography.

To prove that LPTS$_{293-328}$ inhibits tumor cell is due to targeting cell telomere synthesis inhibition, the present inventors used Southern Blot method to detect the telomere length of GFP-LPTS$_{290-328}$/7404, GFP-LPTS/7404, GFP/7404 cells. To analyze telomere length in cells, the FACS-selected cells were collected at the passage numbers indicated by FIG. 4A. Genomic DNA were isolated from the cells and digested with Hinf I and Afa I, and then hybridized with radioactive isotope-labeled probe $^{32}$P-(TTAGGG)$_6$(SEQ ID NO: 10), which is a single-strand DNA repeat sequence (TTAGGG). Telomere length, as shown by autoradiography, was determined by a combination of band intensity and band position, the closer the bands from the upper sample well, the longer the telomeres in the corresponding cells. As shown in FIG. 4A, the telomeres of GFP/7404 control cells remained stable during passage with a length around 4.5 kb. The telomeres of GFP-LPTS/7404 cells were gradually shortened during passage. At the 5$^{th}$ generation passage, the telomeres were shortened to about 3.8 kb. At the 25$^{th}$ generation, the telomeres were shortened to about 2.8 kb. The passage time of GFP-LPTS$_{290-328}$/7404 cells was short, many cells died during culturing. At the 8$^{th}$ generation, the telomeres had been shortened to about 2.5 kb. (FIG. 4B).

Results show that, LPTS290-328 has a very strong telomerase inhibitory activity, and can target telomere synthesis and extension inhibition.

All documents mentioned in the present invention are cited as references in the present application, similar to each document was separately cited as a reference. In addition, it should be understood, by reading the teaching of the present invention, one skilled in the art can change or modify the present invention. However, the equivalent forms also fall within the scope limited by the attached claims.

The invention claimed is
1. A fusion protein, comprising:
 (a) a polypeptide consisting of the amino acid sequence at positions n-328 of SEQ ID NO: 2, wherein n is an integer from 255 to 290; and
 (b) at least one functional protein linked, directly or via a linker peptide, via a peptide bond to the N-terminus of the polypeptide of (a),
 wherein the functional protein comprises 5-500 amino acids,
 wherein the linker comprises 1-20 amino acids.

2. An isolated polynucleotide, characterized in that the polynucleotide comprises a nucleotide sequence that encodes the polypeptide of claim 1.

3. A vector, characterized in that the vector comprises the polynucleotide of claim 2.

4. A genetically engineered host cell, characterized in that the genetically engineered host cell comprises the vector of claim 3.

5. A composition, wherein the composition comprises the fusion protein of claim 1.

6. The composition of claim 5, characterized in that the composition further comprises a material selected from the following: a protein activity promoter, a protein activity stabilizer, and a protein half-life extending preparation.

7. The composition of claim 5, further comprising a pharmaceutically acceptable carrier.

8. A method for preparing the composition of claim 7, comprising: mixing an effective amount of the fusion protein with the pharmaceutically acceptable carrier.

9. A kit, characterized in that the kit comprises the fusion protein of claim 1.

10. The composition of claim 6, further comprising a pharmaceutically acceptable carrier.

11. A method for preparing the composition of claim 10, comprising: mixing an effective amount of the composition with the pharmaceutically acceptable carrier.

12. A kit, characterized in that the kit comprises the composition of claim 6.

13. A kit, characterized in that the kit comprises the composition of claim 7.

14. The fusion protein of claim 1, wherein the at least one functional protein is selected from: a membrane-penetrating protein, a tag protein, a reporter protein, or human IgG1:Fc fragment.

15. The fusion protein of claim 14, wherein the membrane-penetrating protein is Trans-Activator of Transcription (TAT), penetratin, a signal peptide, murine vascular endothelial-cadherin protein (pVEC), transportan, an amphiphilic peptide, or a peptide of nine arginines (Arg9).

16. The fusion protein of claim 14, wherein n is 290.

* * * * *